(12) United States Patent
Whipple

(10) Patent No.: US 9,655,656 B2
(45) Date of Patent: May 23, 2017

(54) MODULAR PEDICLE SCREW ASSEMBLY WITH A SNAP TULIP

(71) Applicant: Amendia, Inc., Marietta, GA (US)

(72) Inventor: Dale Whipple, Acworth, GA (US)

(73) Assignee: Amendia, Inc., Marietta, GA (US)

(*) Notice: Subject to any disclaimer, the term of this patent is extended or adjusted under 35 U.S.C. 154(b) by 29 days.

(21) Appl. No.: 14/600,345

(22) Filed: Jan. 20, 2015

(65) Prior Publication Data

US 2016/0206357 A1    Jul. 21, 2016

(51) Int. Cl.
*A61B 17/70* (2006.01)
*A61B 17/00* (2006.01)

(52) U.S. Cl.
CPC ...... *A61B 17/7037* (2013.01); *A61B 17/7035* (2013.01); *A61B 17/7032* (2013.01); *A61B 17/7034* (2013.01); *A61B 2017/00526* (2013.01)

(58) Field of Classification Search
CPC ............ A61B 17/7001; A61B 17/7032; A61B 17/7034; A61B 17/7035; A61B 17/7037; A61B 17/8665; A61B 17/8695; A61B 17/7038; A61B 17/8605; A61B 2017/867; A61B 2017/868; Y10T 403/32754; F16C 11/069
See application file for complete search history.

(56) References Cited

U.S. PATENT DOCUMENTS

| | | | |
|---|---|---|---|
| 4,701,990 A * | 10/1987 | Kehl | F16C 11/069 29/441.2 |
| 5,176,413 A * | 1/1993 | Westman | 285/321 |
| 6,261,291 B1 * | 7/2001 | Talaber et al. | 606/281 |
| 6,485,491 B1 * | 11/2002 | Farris et al. | 606/250 |
| 8,142,481 B2 | 3/2012 | Warnick | |
| 8,444,681 B2 | 5/2013 | Jackson et al. | |
| 9,216,041 B2 * | 12/2015 | Jackson | A61B 17/7004 |
| 2004/0267264 A1 * | 12/2004 | Konieczynski et al. | 606/73 |
| 2005/0080420 A1 * | 4/2005 | Farris et al. | 606/61 |
| 2006/0155278 A1 * | 7/2006 | Warnick | 606/61 |
| 2006/0161153 A1 * | 7/2006 | Hawkes et al. | 606/61 |
| 2006/0173456 A1 * | 8/2006 | Hawkes et al. | 606/61 |
| 2007/0093827 A1 * | 4/2007 | Warnick | 606/61 |
| 2007/0123862 A1 * | 5/2007 | Warnick | 606/61 |
| 2008/0045955 A1 * | 2/2008 | Berrevoets et al. | 606/61 |
| 2008/0249570 A1 * | 10/2008 | Carson | A61B 17/7038 606/264 |

(Continued)

*Primary Examiner* — Matthew Lawson
*Assistant Examiner* — Amy Sipp
(74) *Attorney, Agent, or Firm* — David L. King

(57) ABSTRACT

A modular head pedicle screw assembly has a bone screw, a tulip, a locking split ring and a saddle. The locking split ring is internal of the tulip positioned in a recess of an inner surface of the tulip. The saddle has a proximal end for engaging a rod and a distal end for receiving the bone screw. The saddle has an exterior surface positioned between the ends. The outer surface is sized to move axially inside the tulip. The saddle expands the locking split ring in an initial pre-loaded position and upon insertion of the tulip over the bone screw, the saddle moves proximally disengaging the locking split ring simultaneously causing the locking split ring to relax to an unexpanded condition while providing tactile and audible feedback to the surgeon and locking the bone screw into the tulip.

6 Claims, 9 Drawing Sheets

(56) References Cited

U.S. PATENT DOCUMENTS

| | | | |
|---|---|---|---|
| 2008/0249576 A1* | 10/2008 | Hawkes | A61B 17/7037 606/305 |
| 2009/0318978 A1* | 12/2009 | Podgorski et al. | 606/290 |
| 2011/0077694 A1* | 3/2011 | Biedermann et al. | 606/305 |
| 2011/0098755 A1* | 4/2011 | Jackson | A61B 17/7008 606/305 |
| 2012/0046700 A1 | 2/2012 | Jackson et al. | |
| 2012/0059426 A1 | 3/2012 | Jackson et al. | |
| 2012/0209336 A1* | 8/2012 | Jackson et al. | 606/305 |
| 2013/0072981 A1* | 3/2013 | Jackson et al. | 606/263 |
| 2013/0103098 A1* | 4/2013 | Jackson et al. | 606/305 |
| 2013/0110180 A1* | 5/2013 | Doubler | A61B 17/7037 606/308 |
| 2013/0184766 A1* | 7/2013 | Black | A61B 17/8047 606/289 |
| 2013/0345754 A1* | 12/2013 | Doubler | A61B 17/7037 606/266 |
| 2014/0058454 A1* | 2/2014 | Hammer et al. | 606/279 |
| 2014/0094849 A1* | 4/2014 | Spratt et al. | 606/257 |
| 2014/0236239 A1* | 8/2014 | Biedermann | A61B 17/7037 606/278 |
| 2014/0296925 A1* | 10/2014 | Lawson et al. | 606/289 |
| 2015/0173816 A1* | 6/2015 | Biedermann et al. | A61B 17/8605 |
| 2015/0182260 A1* | 7/2015 | Jackson et al. | A61B 17/7037 |
| 2015/0201972 A1* | 7/2015 | Doubler et al. | A61B 17/7037 |
| 2015/0351807 A1* | 12/2015 | Jackson | A61B 17/702 606/277 |
| 2015/0351809 A1* | 12/2015 | Jackson | A61B 17/7037 606/266 |

\* cited by examiner

MODULAR PEDICLE SCREW ASSEMBLY WITH A SNAP TULIP

TECHNICAL FIELD

The present invention relates to an improved modular head pedicle screw assembly.

BACKGROUND OF THE INVENTION

Bone anchor screws come in a variety of shapes and sizes. One of the more common styles has a polyaxial head that allows for the screw to enter the bone structure at an ideal or preferred inclination. To achieve this polyaxial inclination, the head has a shape configured to rotate about its lower external surface. This lower surface can be one of a number of shapes like conical or spherical or hemispherical. This ability is often used in devices having a modular head assembly.

The modular head pedicle screw assembly generally includes a tulip. A tulip is a body structure having two opposing sides spaced by a slotted opening to receive a spinal rod. The tulip often employs internal threads to receive a rod locking set screw to anchor or fix the rod in the tulip. The lower portion of the tulip has an opening to receive the pedicle screw in a base seat. Often, the tulip can have a saddle that both supports the rod along an underside of the rod. The saddle having an upper recessed curvature into which the rod sits and a lower cup like opening to receive the top of the pedicle screw head. When the saddle and rod and set screw are tightened, the screw angle is fixed against the tulip seat.

Often, it is preferred that the pedicle screw is first placed securely in the bone structure leaving the head protruding above the bone surface. In this surgical procedure the tulip assembly must be adapted to fit down onto the projecting screw head. To accomplish this, the surgeon must push the tulip onto and over the screw head without a clear path of vision. Accordingly, the placement must be accomplished without any way of knowing if the tulip or other device is properly secured. Thereafter, the device is tightened to complete the assembly and the only way to insure the assembly is secure requires an upward pulling of the tightened assembly. This is not a good test the assembly will be loosened or the screw to bone interface weakened.

It is, therefore, an objective of the present invention to provide a way for a surgeon to place a tulip assembly onto a pedicle screw in such a way the surgeon knows he has made a proper and secure connection.

It is a further objective that the device alerts the surgeon that he has properly fitted the tulip onto the pedicle screw head. It is another objective that the device provides a self-locking feature that when activated by assembly the surgeon can tactilely feel the lock engagement and audibly hear it insuring he has made a proper assembly. These and other objectives are achieved by the invention as described hereinafter.

SUMMARY OF THE INVENTION

A modular head pedicle screw assembly has a bone screw, a tulip, a locking split ring and a saddle. The locking split ring is internal of the tulip positioned in a recess of an inner surface of the tulip. The saddle has a proximal end for engaging a rod and a distal end for receiving the bone screw. The saddle has an exterior surface positioned between the ends. The outer surface is sized to move axially inside the tulip. The saddle expands the locking split ring in an initial pre-loaded position and upon insertion of the tulip over the bone screw, the saddle moves proximally disengaging the locking split ring simultaneously causing the locking split ring to relax to an unexpanded condition while providing a tactile feedback to the surgeon and locking the bone screw into the tulip. The release of the locking split ring also produces an audible sound.

The recess of the tulip has a conical surface tapering inward distally. The relaxed outer diameter of the locking split ring is larger than the distal opening of the tulip.

The bone screw has one of the following head shapes; at least partially a hemispherical or spherical head, conical or a radial array or loci of cylindrical surfaces or any other bulbous head. The head has a driving feature for torsionally driving the screw into bone.

A method of assembling a tulip comprises the step of providing a tulip; and positioning a locking split ring inside the tulip in pre-loaded expanded condition. The method also includes the step of positioning the locking split ring on a saddle inside the tulip to pre-load in the expanded condition. The method also includes the step of inserting the locking split ring into the tulip in a relaxed or contracted condition prior to pre-loading in an expanded condition.

BRIEF DESCRIPTION OF THE DRAWINGS

The invention will be described by way of example and with reference to the accompanying drawings in which.

DETAILED DESCRIPTION OF THE INVENTION

Figure 4A:
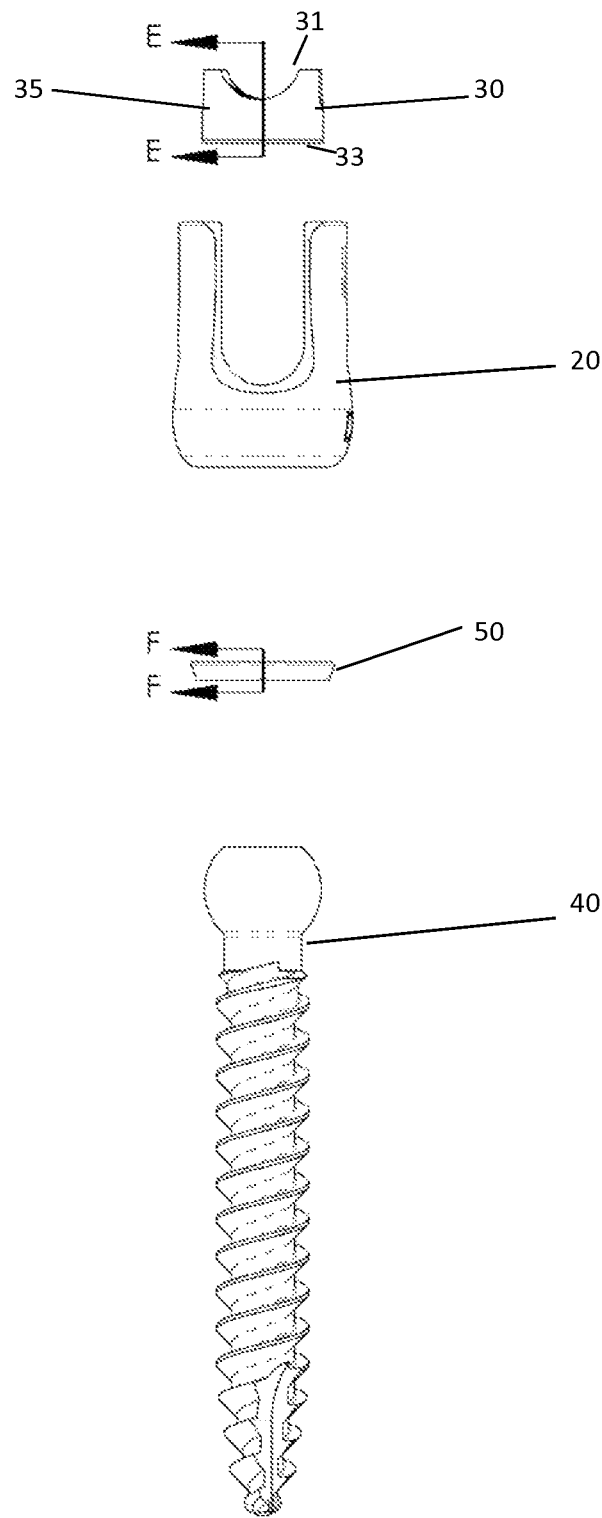
FIG. 4A is an exploded cross sectional view of the assembly showing the tulip, the saddle, the locking split ring and the pedicle screw.
Figure 4B:
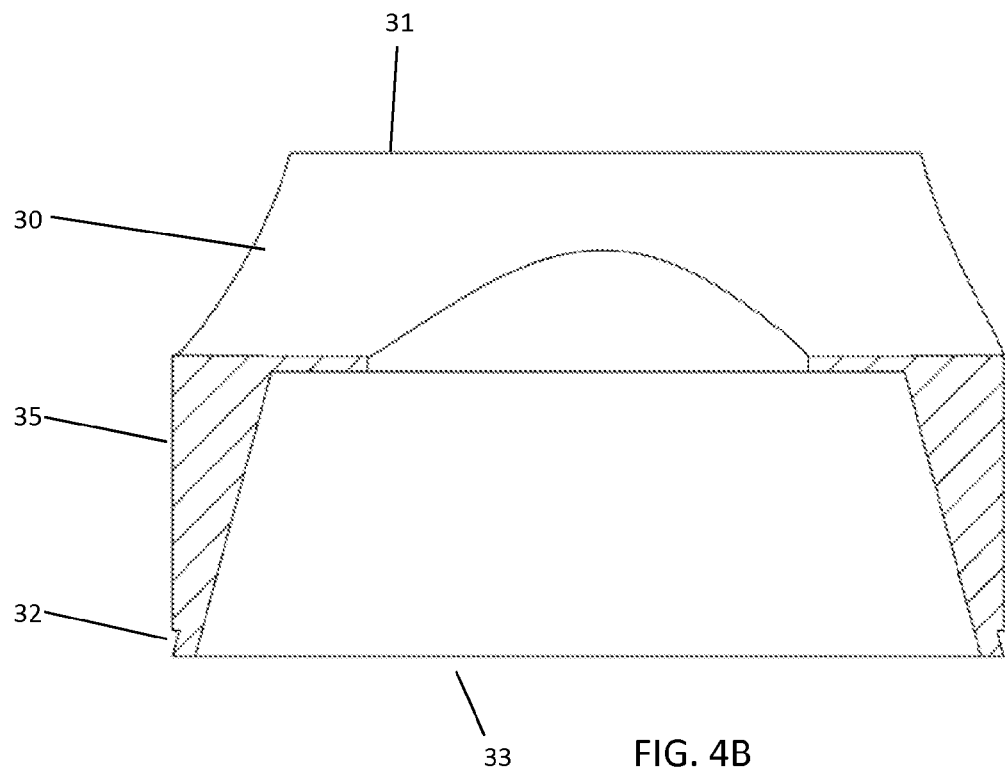
FIG. 4B is an enlarged cross sectional view of the saddle.

With reference to FIG. 4A, an exploded view of a modular head pedicle screw assembly is illustrated. The modular head pedicle screw assembly has a bone screw 40, a tulip 20 and a locking split ring 50 internal of the tulip positioned and held in a recess 22 of an inner surface of the tulip 20. The assembly further includes a saddle 30 having a proximal end 31 for engaging a rod and a distal end 33 for receiving a bone screw. The saddle 30 has an exterior surface 35 positioned between the ends. The outer surface 35 is sized to move axially inside the tulip 20. The saddle 30 expands the locking split ring 50 in an initial pre-loaded position where it is held in an exterior recess or a groove 32 and upon insertion of the tulip 20 over a bone screw 40, the saddle 30 moves proximally disengaging the locking split ring 50 simultaneously causing the locking split ring 50 to relax in an unexpanded condition while providing a tactile feedback to the surgeon and simultaneously locking the head 42 of the bone screw 40 into the tulip 20. Upon release of the locking split ring 50, an audible sound may also be heard as the ring 50 snaps against the head 42 of the bone screw 40.

Figure 1A:
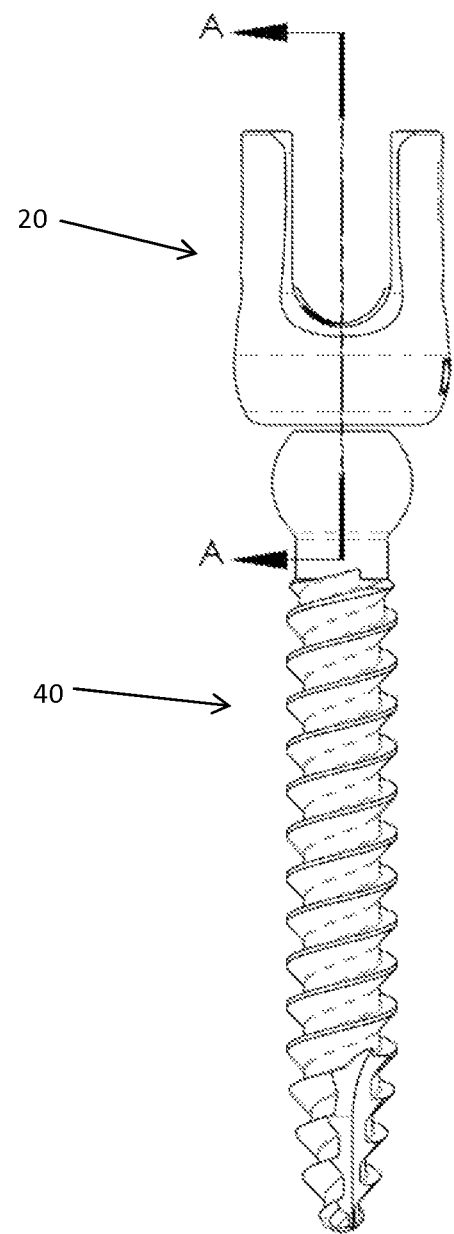
FIG. 1A is a plan view of the modular head pedicle screw assembly prior to the tulip assembly connection of the pedicle screw.
Figure 1B:
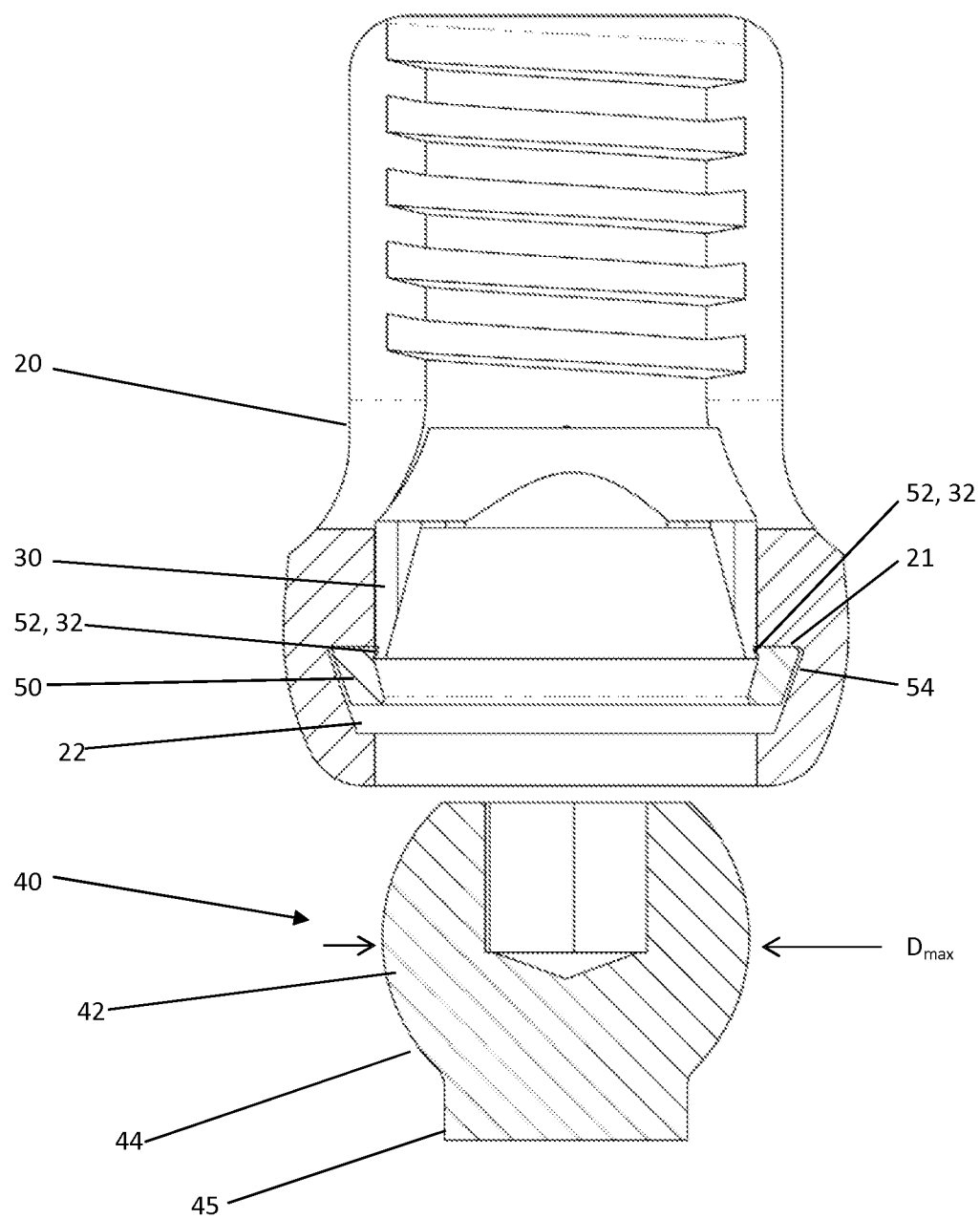
FIG. 1B is an enlarged cross sectional view of an upper portion of the modular head pedicle screw assembly prior to the tulip assembly connection of the pedicle screw.
Figure 2A:
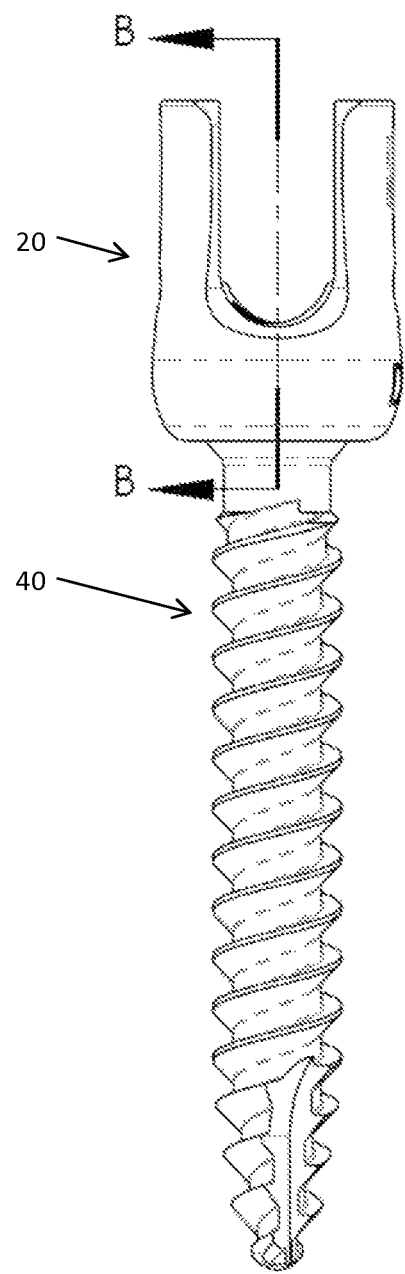
FIG. 2A is a plan view of FIG. 1 showing the pedicle screw assembled to the tulip moving the saddle upwardly inside the tulip as the locking split ring disengages from the saddle.
Figure 2B:
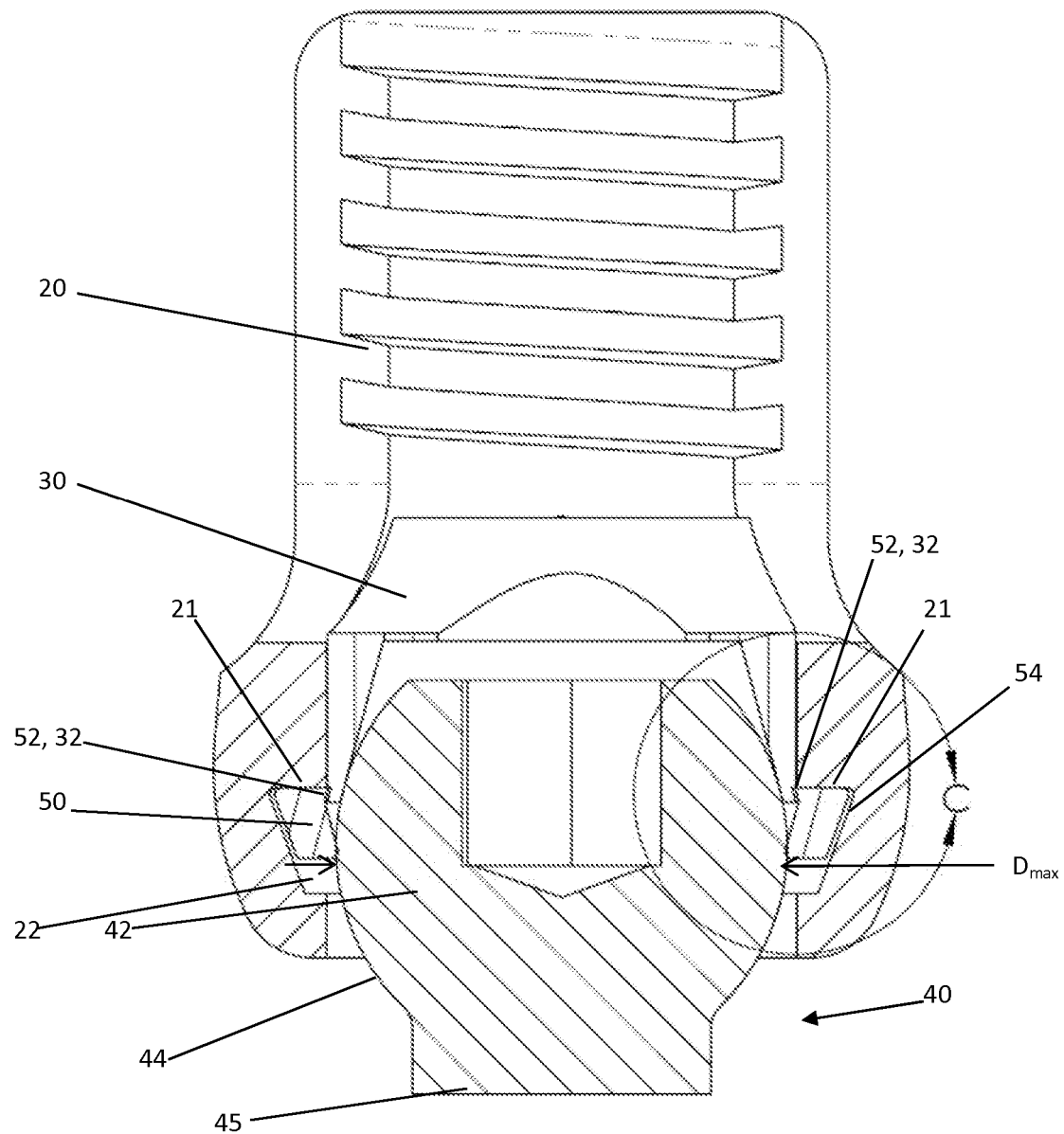
FIG. 2B is an enlarged cross sectional view of the pedicle screw head inside the saddle with the snap ring expanded on the saddle.
Figure 2C:
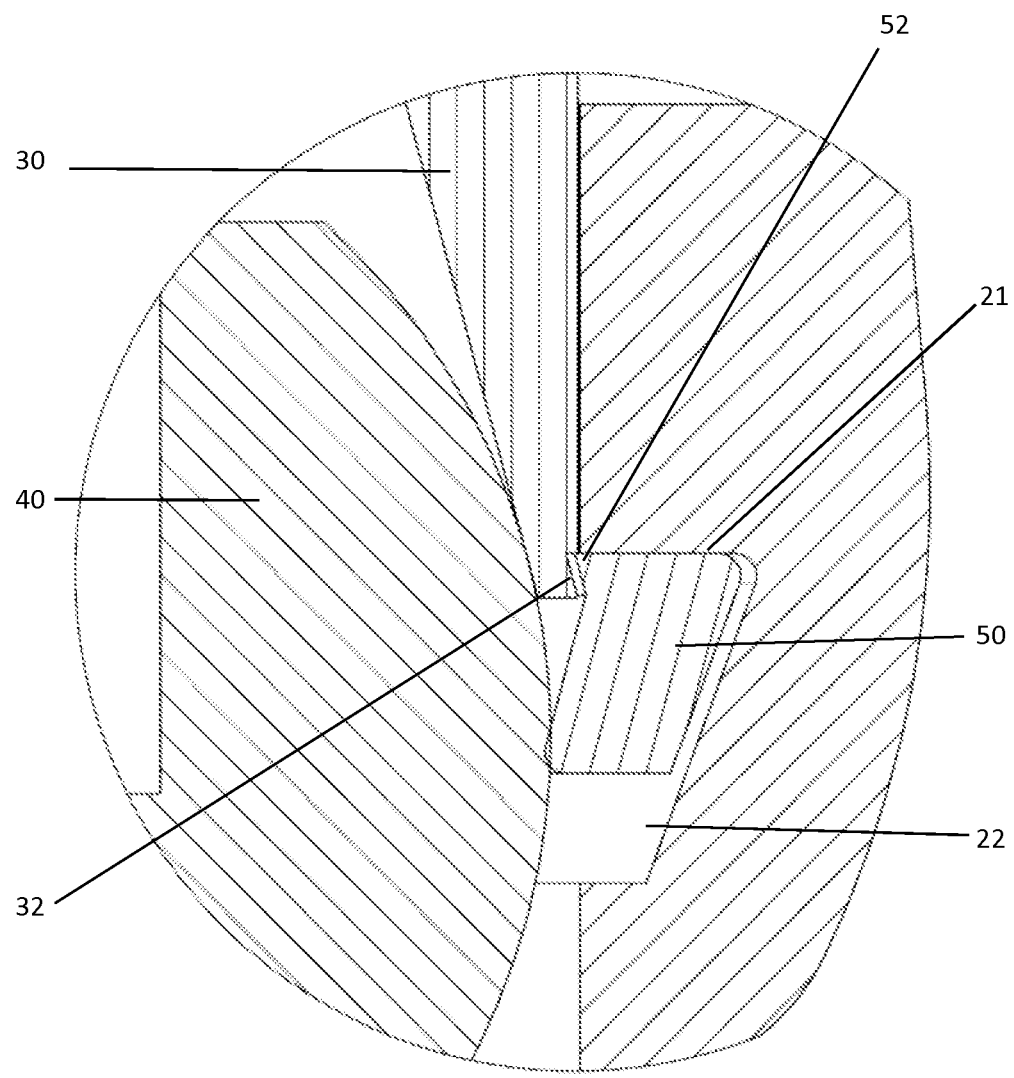
FIG. 2C is a larger view from FIG. 2B showing the locking split ring expanded and moved upwardly in the tulip by the screw head.
Figure 3A:
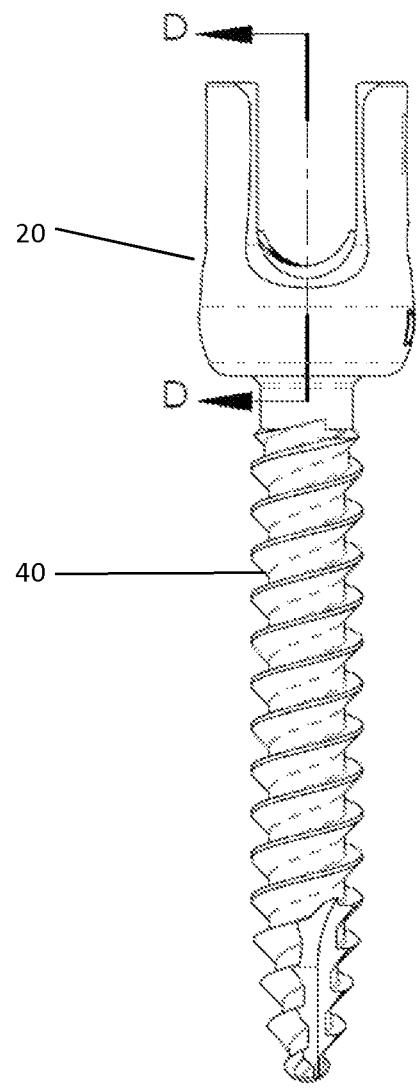
FIG. 3A is the view showing the pedicle being firmly secured by the locking split ring.
Figure 3B:
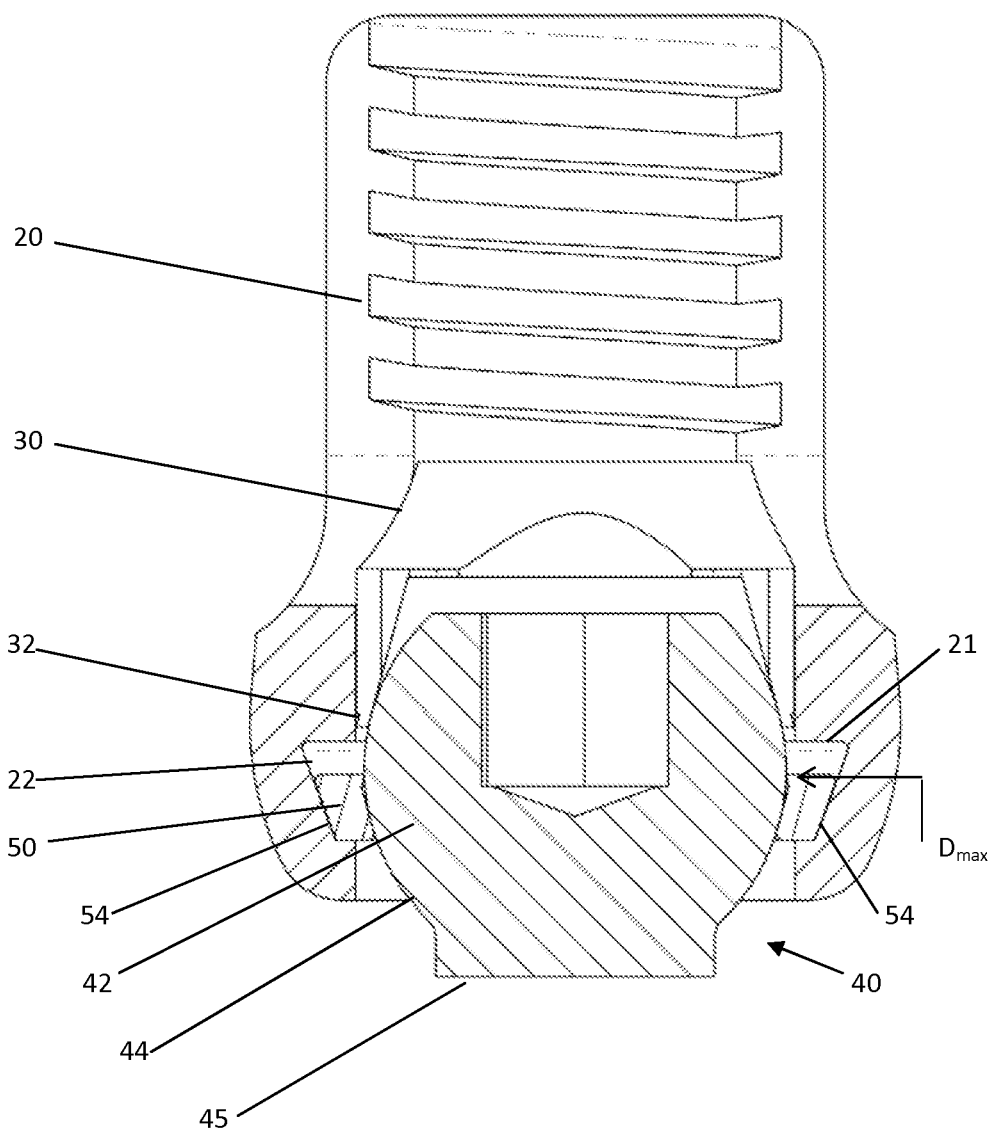
FIG. 3B is an enlarged cross sectional view showing the pedicle screw locked by the locking split ring which is contracted after disengaging the saddle.

With reference to FIGS. 1A-3B, the assembly of the modular head pedicle screw assembly onto a pedicle screw 40 is illustrated. Initially, the tulip 20 with a saddle 30 having a pre-loaded locking split ring 50 assembled onto it and held inside the tulip 20 in a conically inwardly tapered recess or groove 22 is shown best in FIGS. 1B, 2B and 2C. As the tulip assembly is pushed onto the head 42 of the pedicle screw 40, the saddle 30 moves upwardly causing the locking split ring 50 to disengage from an exterior recess or groove 32 on the saddle 30, by causing the locking split ring 50 to be abutted against an upper surface 21 of the tulip 20. As this occurs, the locking split ring 50 which is tensioned in the expanded condition and has a mating projection or ridge 52 configured to fit into the recess or groove 32 of the saddle 30 which is released from recess 32 on the saddle 30 and the energy that was stored in the locking split ring 50 in the expanded condition is released causing the locking split ring 50 to snap against the exterior surface 44 of the head 42 of the pedicle screw 40. When this release occurs, this energy reduction can be felt by the surgeon as he is pushing the tulip 20 against the pedicle screw 40 head 42. As the locking split ring 50 contacts the head 42 it also makes an audible sound striking surface 44 of the head 42 with a sufficient amount of force to create a noise. This is best illustrated in FIG. 3B. The surgeon is both able to feel the release of the locking split ring 50 from the saddle 30 and simultaneously hear the locking of the split ring 50 against a lower portion of the surface 44 of the pedicle screw 40 head 42. When this occurs, the surgeon has confidence that the assembly has been properly mounted in such a fashion that the tulip 20 is securely held onto the bone screw 40. Advantageously, the force needed to release the already expanded ring 50 from the saddle 30 is far less than the forces that are required to push the head 42 of a bone screw 40 through a split ring 50 using the screw head 42 to expand a locking ring 50. This means the forces on a bone screw 40 are greatly reduced from those found in prior art devices.

The bone screw 40 can be fully engaged in a pre-existing bone and therefore the head 42 of the pedicle screw 40 is positioned exposed outward of the bone. This allows the addition of the tulip 20 assembly to be made without the surgeon needing to see the tulip 20 and head 42 engage as he will feel and hear the locking of the locking split ring 50 against the surface 44 of pedicle screw 40 head 42. This tactile sensation provides the surgeon with the confidence that when he has assembled the tulip 20 onto the pedicle screw 40 it will be securely locked in position as the saddle 30 will disengage the pre-tensioned locking split ring 50 such that it enables the energy forces to be transmitted to the pedicle screw 40 and the surgeon can feel this condition.

Figure 4C:
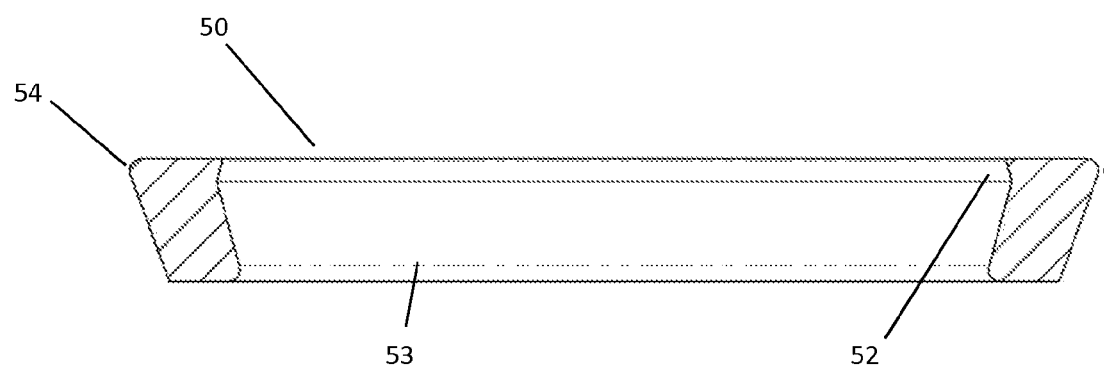
FIG. 4C is an enlarged cross sectional view of the split ring.

Accordingly, for this device to be manufactured, it is important that the locking split ring 50 shown in FIG. 4A is assembled into a distal opening in the tulip 20. Inside the distal opening is a tapered or conical recess 22 that tapers inwardly toward the distal end. Due to the size of the split ring 50, it is important that on initial assembly, that the split ring is inserted into the distal end preferably by being contracted slightly as it is pushed through an opening smaller than the size of the outer diameter of the split ring 50. Once the split ring 50 is inside the tulip 20, it can be released in a relaxed condition. At this point, the saddle 30 can be positioned inside the tulip 20 and slid down to engage the split ring 50. The split ring 50 is then expanded with a tool or other device, not shown, and positioned onto the distal end of the saddle 30. The distal end of the saddle 30 will have a recess or groove or flat 32 ideally adapted to hold the locking split ring 50 in the expanded position. Once this assembly of the locking split ring 50 to the saddle 30 is achieved, the locking split ring 50 is in an open position such that upon insertion of the pedicle screw 40 into the saddle 30, as previously described, it can become disengaged. The locking split ring 50 is preferably made of a high strength alloy having a very low creep percentage. This insures the energy stored at assembly is available to be released when the expanded ring 50 is disengaged from the saddle 30. The ring 50 is preferably made of titanium or a high strength stainless steel. As shown in FIG. 4C, the split ring 50 has ridge or projection 52.

Accordingly, during manufacture, the tulip 20, saddle 30 and locking split ring 50 are pre-loaded as an assembly and the pedicle screws 40 are provided separately such that they can be assembled either with the screw already in the bone or it can be assembled separately as required. As illustrated, the saddle 30 has an opening through which the pedicle screw 40 can be tightened or torqued down as required. These openings can be flats that are in a recess or can be any means for providing a torsional tightening of a pedicle screw into bone.

As illustrate, the tulip 20 has parallel walls that are opposing, the internal surface of the tulip 20 has threads for engaging a set screw. The tulip 20, as configured, is designed with a slotted opening for receiving a spinal rod or other similar mechanical device that can be positioned onto the upper surface of the saddle 30 which has a complimentary curved concavity for receiving a round or circular rod as illustrated. Once the set screw is put into position on top of the rod, the rod is then securely fastened against the saddle 30. Once this assembly is achieved, the polyaxial feature of the set screw is locked into position at the desired location.

These polyaxial features of the screw 40 are well understood in the art. It is important that the pedicle screw 40 have at least a partially hemispherical, spherical head 42 such that the lower head surface 44 is engaged by the tulip 20 and locking split ring 50 such that the screw 40 can be rotated in a polyaxial direction. This can be accomplished as indicated by hemispherical, a spherical head, a conical head or a radial array of loci or cylindrical surfaces or any other bulbous head configuration that is adapted to move in a polyaxial direction when inserted inside a tulip 20. Preferably, the screw 40 is made of an implantable metal such as stainless steel or, more preferably, titanium.

With reference again to FIGS. 1B-3B, the head 42 of the pedicle screw 40 has a maximum diameter $D_{max}$ and this diameter decreases above and below this maximum $D_{max}$. Most particularly, in the exemplary screw 40, the lower portion 44 of the screw head 42 hemispherical external surface, decreases in size. When the screw 40 starts to move the saddle 30 with the pre-loaded locking split ring 50 affixed, the head 42 enters the saddle opening and prior to the split ring being engaged from the saddle by abutting the tulip 20 at surface 21, the maximum diameter $D_{max}$ is shown above the inside diameter of the split ring 50. Accordingly, when the split ring 50 is freed, the ring 50 contracts as the ridge or projection 52 and the inside diameter 53 slide against this lower portion 44 toward the screw shank 45. As this movement occurs, the tapered conical shaped recess 22 inside the tulip 20 comes into contact with the outer diameter 54 of the locking split ring 50 causing the tulip 20 to move slightly toward the screw shank 45, as shown in FIG. 3B. This subtle, but very quick motion is felt by the surgeon who is pushing the tulip 20 over the screw head 42. The sensation is similar to an assisting force moving the assembly into a locked position. The conical recess 22 diametrically tapers decreasing in size distally causing the locking split ring 50 to slide against it as it moves downward on the lower portion 44 of the screw head 42.

All this movement occurs as the energy stored in the expanded locking split ring 50 is released and the abutting and contracting ring 50 rapidly moves to a self-locking position. The combination of this rapid energy release creates an audible snapping sound and motions transmitted to the surgeon alerting him that the assembly is properly positioned and securely locked in place. The benefit is of this all occurring without requiring an expansion of the locking split ring 50 which can take sizable effort. The assembly being pre-loaded at the factory with the ring 50 pre-positioned on the saddle 30 allows the ring 50 to be substantially stronger than otherwise possible because the forces to disengage the locking ring 50 are far less than those required to stretch it over a pedicle screw head 42.

The exemplary screw 40 was an 8.5 mm screw. The invention can be of any suitable size for the required purpose.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A modular head polyaxial pedicle screw assembly comprising:
   a bone screw, the bone screw having a polyaxial at least partially spherical head with a driving feature at a proximal end to tighten the screw into bone and a threaded shank;
   a tulip assembly configured to be pushed onto the head of the bone screw, the tulip assembly comprising:
   a tulip configured to have parallel walls that are opposing defining a slotted opening configured for receiving a spinal rod, opening walls of the tulip having a thread configured to receive a set screw, the tulip having a recess on an inner surface of the tulip configured to receive a locking split ring, the recess having an upper surface;
   a locking split ring internal of the tulip positioned in the recess of the inner surface of the tulip, the locking split ring having a relaxed inner diameter and a relaxed outer diameter in an unexpanded position or condition;
   a saddle having a proximal end with a concavity for engaging the spinal rod and a distal end for receiving the bone screw, the saddle having an opening through which the driving feature of the bone screw can be accessed, the saddle having an exterior surface positioned between the ends and an exterior recess or groove to which the locking split ring can be affixed when expanded, the exterior surface being sized to be inserted through a distal opening of the tulip and positioned below the thread of the opening walls of the tulip to move axially inside the tulip; and
   wherein the saddle holds the locking split ring in an initial pre-loaded expanded position at the exterior recess or groove and, upon insertion of the tulip assembly over the bone screw, the saddle moves proximally, which causes the locking split ring to abut the upper surface of the recess of the tulip, this abutting disengages the locking split ring from the exterior recess or groove of the saddle, thereby releasing the locking split ring from the saddle and causing the inner diameter to reduce to the relaxed unexpanded condition upon release of energy which causes the locking split ring to snap against and simultaneously slide along an exterior surface of a lower portion of the polyaxial at least partially spherical head of the bone screw between a maximum diameter of said polyaxial at least partially spherical head and the shank of the bone screw, wherein the snap provides a tactile feedback to a surgeon and further provides a locking of the locking split ring in the unexpanded position or condition against the lower portion of the exterior surface of the head of the bone screw inside the tulip, wherein the relaxed outer diameter of the locking split ring is larger than the distal opening of the tulip allowing the locking split ring to affix the tulip to the bone screw in a locked and loaded position while providing a polyaxially movable condition of the bone screw relative to the tulip and, upon engaging the rod into the concavity of the saddle and inserting and tightening the set screw, the bone screw movement relative to the tulip is locked in position as the head is fixed between the saddle and the disengaged lock ring at the distal opening of the tulip.

2. The modular head pedicle screw assembly of claim 1 wherein the release of the locking split ring also produces an audible sound as the locking split ring snaps against the exterior surface of the lower portion of the head of the bone screw.

3. The modular head pedicle screw assembly of claim 1 wherein the recess of the tulip has a conical surface tapering inward distally.

4. A method of assembling a tulip comprises the step of:
   providing a tulip and a saddle as a tulip assembly, the tulip assembly configured to be pushed onto a head of a bone screw, the tulip configured to have parallel walls that are opposing defining a slotted opening configured for receiving a spinal rod, opening walls of the tulip having a thread configured to receive a set screw, thread configured to receive a set screw, the tulip having a recess on an inner surface of the tulip configured to receive a locking split ring, the recess having an upper surface; the locking split ring internal of the tulip positioned in the recess of the tulip, the locking split ring having a relaxed inner diameter and a relaxed outer diameter in an unexpanded position or condition; the saddle having a proximal end with a concavity for engaging the spinal rod and a distal end for receiving the bone screw, the saddle having an opening through which a driving feature of the bone screw can be accessed, the saddle having an exterior surface positioned between the ends and an exterior recess or groove to which the locking split ring can be affixed when expanded, the exterior outer surface being sized to be inserted through a distal opening of the tulip and positioned below the threads of the opening walls of the tulip to move axially inside the tulip and wherein the saddle holds the locking split ring in an initial pre-loaded expanded position at the exterior recess or groove and upon insertion of the tulip over the bone screw, the saddle moves proximally, which causes the locking split ring to abut the upper surface of the recess of the tulip, this abutting disengages the locking split ring from the exterior recess or groove of the saddle, thereby releasing the locking split ring from the saddle and causing the inner diameter to reduce to the relaxed unexpanded condition upon release of energy, which causes the locking split ring to snap against and simultaneously slide along an exterior surface of a lower portion of a polyaxial at least partially spherical head of the bone screw between a maximum diameter of said polyaxial at least partially spherical head and a shank of the bone screw, wherein the snap provides a tactile feedback to a surgeon and further provides a locking of the locking split ring in the unexpanded position or condition against the lower portion of the exterior surface of the head of the bone screw inside the tulip, wherein the relaxed outer diameter of the locking split ring is larger than the distal opening of the tulip allowing the locking split ring to affix the tulip to the bone screw in a locked and loaded position while providing a polyaxially movable condition of the bone screw relative to the tulip and, upon engaging the rod into the concavity of the bone screw relative to the tulip and upon engaging the rod into the concavity of the saddle and inserting and tightening the set screw, the bone screw movement relative to the tulip is locked in position as the head is fixed between the saddle and the disengaged lock ring at the distal opening of the tulip; and positioning the locking split ring inside the tulip and onto the saddle to complete the tulip assembly in the pre-loaded expanded condition.

5. The method of assembling a tulip of claim 4 the step of positioning the locking split ring also includes the step of positioning the saddle inside the tulip to pre-load in the expanded condition.

6. The method of assembling a tulip of claim 5 also includes the step of inserting the locking split ring into the tulip in the relaxed or a contracted condition prior to pre-loading the snap ring onto the exterior recess or groove of the saddle in the expanded condition.

* * * * *